(12) United States Patent
Cho

(10) Patent No.: US 7,578,172 B2
(45) Date of Patent: Aug. 25, 2009

(54) SYMMETRICAL VISCOSITY SENSOR

(75) Inventor: Jin Hee Cho, Suwon-si (KR)

(73) Assignee: Hyundai Motor Company, Seoul (KR)

( * ) Notice: Subject to any disclaimer, the term of this patent is extended or adjusted under 35 U.S.C. 154(b) by 263 days.

(21) Appl. No.: 11/648,875

(22) Filed: Dec. 29, 2006

(65) Prior Publication Data

US 2008/0092637 A1 Apr. 24, 2008

(30) Foreign Application Priority Data

Oct. 18, 2006 (KR) ............... 10-2006-0101448

(51) Int. Cl.
*G01N 11/10* (2006.01)
(52) U.S. Cl. ..................... 73/54.24; 73/54.27
(58) Field of Classification Search ............... 73/54.24, 73/54.25, 54.26, 54.27, 54.21; 702/50
See application file for complete search history.

(56) References Cited

U.S. PATENT DOCUMENTS 4,644,482 A * 2/1987 Juanarena ............... 702/98

| 5,670,709 | A | * | 9/1997 | Gallagher |
| 6,247,354 | B1 | | 6/2001 | Vig et al. |
| 6,450,013 | B1 | * | 9/2002 | Gallagher |
| 6,813,935 | B2 | * | 11/2004 | Gallagher |

FOREIGN PATENT DOCUMENTS

| JP | 53-107881 | 9/1978 |
| JP | 06-148055 | 5/1994 |
| JP | 11-094726 | 4/1999 |

* cited by examiner

*Primary Examiner*—Hezron Williams
*Assistant Examiner*—Nathaniel Kolb
(74) *Attorney, Agent, or Firm*—Morgan, Lewis & Bockius LLP

(57) ABSTRACT

A symmetrical viscosity sensor for measuring the viscosity of fluids such as transmission oil or engine oil. Torsion oscillators are arranged symmetrically on both sides. The viscosity sensor includes a coupling shaft; a torsion oscillator coupled symmetrically to both ends of the coupling shaft; at least one insulator coupled to a center portion of said coupling shaft; a plurality of oscillation means arranged between each torsion oscillator and the insulator; a signal transmission/reception line for transmitting and receiving a driving and detection signal of said oscillation means; and a control unit for controlling said driving and detection signal via said signal transmission/reception line.

9 Claims, 9 Drawing Sheets

Deteriorated oil 5W30
after Vehicle A runs 12,500km, 5W30+diesel fuel(2-10%)

SYMMETRICAL VISCOSITY SENSOR

CROSS-REFERENCE TO RELATED APPLICATION

This application claims priority to and benefit of Korean Patent application No. 10-2006-0101448 filed on Oct. 18, 2006, in the Korean Intellectual Property Office, the disclosure of which is incorporated herein by reference.

BACKGROUND OF THE INVENTION

1. Field of the Invention

The present invention relates to a symmetrical viscosity sensor, and in particular, to a symmetrical viscosity sensor for measuring the viscosity of fluids such as transmission oil or engine oil, in which the torsion oscillators are arranged symmetrically on both sides so that the viscosity may be measured effectively due to oscillations within the elastic range as the sensing effective areas increase.

2. Description of the Related Art

Generally, a viscosity sensor for measuring the viscosity of transmission oil or engine oil is mounted in an oil path. The viscosity sensor can be used to indicate when the oil should be replaced.

Japanese Laid-Out Patent No. 1978-107881 describes a viscosity measuring apparatus in which the oscillation plates of a circle shape are arranged oppositely, and the U.S. Pat. No. 6,247,354 describes a sensor for detecting the fluid property in which the resonators of the piezoelectric plate functioning as a sensor unit are formed as a pair.

In addition, Japanese Publication Patent No. 1994-148055 describes a viscosity measuring apparatus in which an oscillation unit corresponding to a sensor unit is formed as a pair. But, since each oscillation unit of these patents generates simple oscillation, there is a drawback that the viscosity measuring results for the fluids are not accurate.

The above information disclosed in this Background section is only for enhancement of understanding of the background of the invention and therefore it may contain information that does not form the prior art that is already known in this country to a person of ordinary skill in the art.

SUMMARY OF THE INVENTION

The present invention relates to a symmetrical viscosity sensor which can measure the viscosity of fluids such as transmission oil or engine oil. Since the torsion oscillators are arranged symmetrically on both sides, as the sensing effective areas increase, the viscosity can be measured effectively due to oscillations within the elastic range.

Embodiments of the present invention provides a symmetrical viscosity sensor comprising a coupling shaft; a torsion oscillator symmetrically coupled to each end of the coupling shaft; first and second insulators inserted into and coupled to a center portion of said coupling shaft; a plurality of oscillation means which are embedded between said torsion oscillator of left and right side, and each insulator; a signal transmission/reception line for transmitting and receiving a driving/detection signal of said oscillation means; and a control unit for controlling said driving and detection signal via said signal transmission/reception line.

DETAILED DESCRIPTION OF THE PREFERRED EMBODIMENTS

Figure 1A:
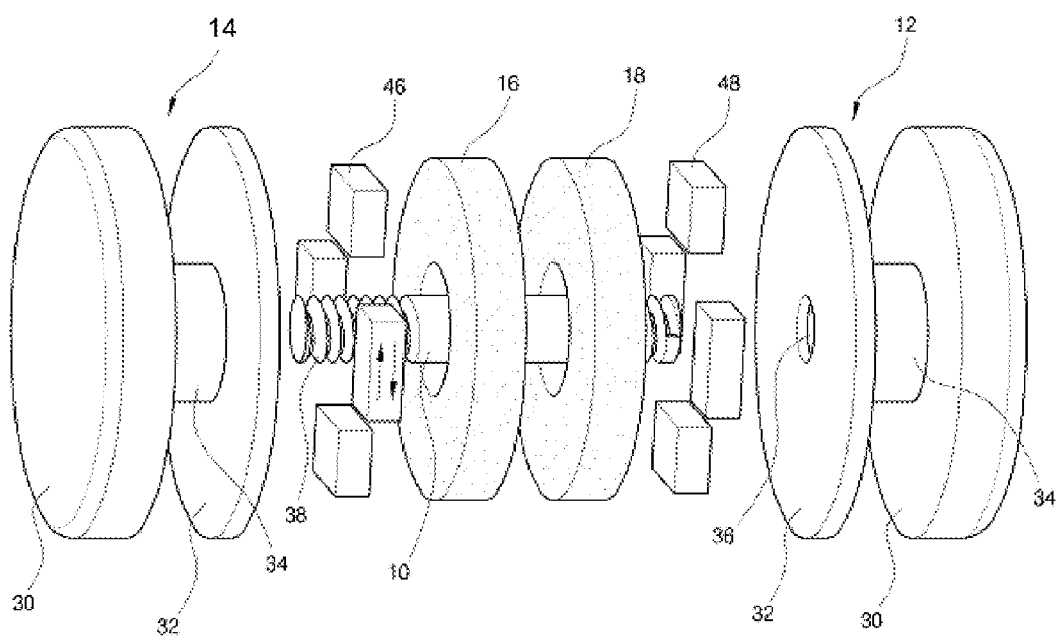
FIG. 1a and FIG. 1b illustrate a disconnected symmetrical viscosity sensor according to an embodiment of the present invention.

The present invention provides a symmetrical viscosity sensor arranged symmetrically so that signals inputted from outside may be exchanged while an insulator is arranged between a torsion oscillator and an oscillation means.

In an exemplary embodiment, the torsion oscillator is coupled symmetrically to both ends of a coupling shaft, said insulator is inserted into and coupled to a center portion of said coupling shaft, and a plurality of oscillation means are arranged between said torsion oscillator and each insulator. A signal transmission/reception line transmits and receives a driving and detection signal of said oscillation means; and a control unit controls said driving and detection signal via said signal transmission/reception line.

In a further embodiment, an inside case is provided for protecting said torsion oscillators, the first and second insulators, said oscillation means, and said signal transmission/reception line. A plastic injection case may further surround said inside case.

In a further embodiment, said control unit further comprises a printed circuit board which is built in a upper side of said plastic injection case and is connected to said signal transmission/reception line for exchange of the signals, and a micro-computer for receiving a signal transmitted from said printed circuit board.

In a further embodiment, said torsion oscillator has a symmetrical structure formed by a stainless material, and comprises an exterior torsion oscillation plate exposed to outside of said plastic injection case; an inside torsion oscillation plate built in an inside case of said plastic injection case; and an oscillation shaft which is connected to said exterior torsion oscillation plate and said inside torsion oscillation plate, and thereby is exposed to outside of said plastic injection case.

In a further embodiment, a female screw thread, to which a male screw thread processed at each end of said coupling shaft can be coupled, is formed on a center portion of an inner side of each inside torsion oscillation plate.

In a further embodiment, said signal transmission/reception line comprises a power supply line for driving said oscillation means; and a signal detection line for receiving a detection signal of said oscillation means.

In a further embodiment, said oscillation means comprises a plurality of piezoelectric elements for reception in between said insulator and one of the inside torsion oscillators, receiving a signal from said power supply line and oscillating; and a plurality of piezoelectric elements for transmission in between said insulator and the other inside torsion oscillator, and transmits a signal to said printed circuit board via said signal detection line.

In a further embodiment, said piezoelectric elements are disposed in said inside torsion oscillator and said insulator, and all four elements are arranged with an equal space between them along the circumferential direction of said coupling shaft.

A symmetrical viscosity sensor of an embodiment of the present invention has a complete symmetrical structure in which torsion oscillators 12, 14 are arranged symmetrically.

The torsion oscillators 12, 14 are made of a stainless material. Each comprises an exterior torsion oscillation plate 30, an inside torsion oscillation plate 32 having a thickness less than that of the exterior torsion plate, and an oscillation shaft. A female screw thread 36 is provided in the inside torsion plate 32.

The torsion oscillators 12, 14 are connected to each other by a coupling shaft 10 on which a male screw thread 38 is provided on both ends thereof. The male screw thread 38 is attached to the female screw thread 36 of the inside torsion oscillation plate 32 of the torsion oscillators 12, 14. A first insulator 16 and a second insulator 18 are coupled to the coupling shaft 10, and these insulators 16, 18 prevent contacts and shorts between a piezoelectric element 46 for reception, and a piezoelectric element 48 for transmission of the oscillation means, which will be described later.

Figure 1B:
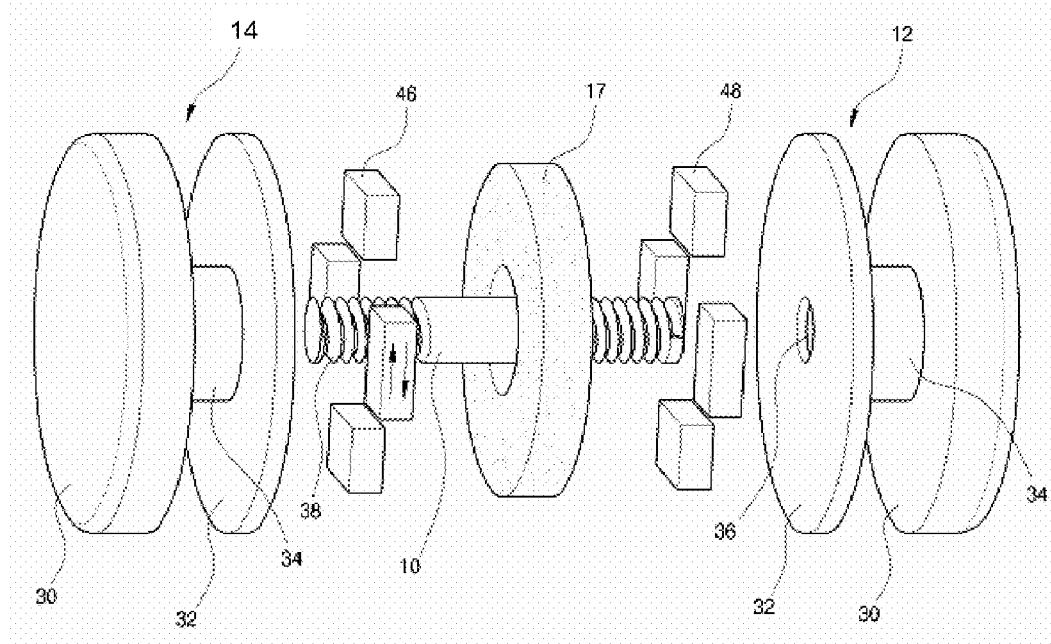
Figure 2:
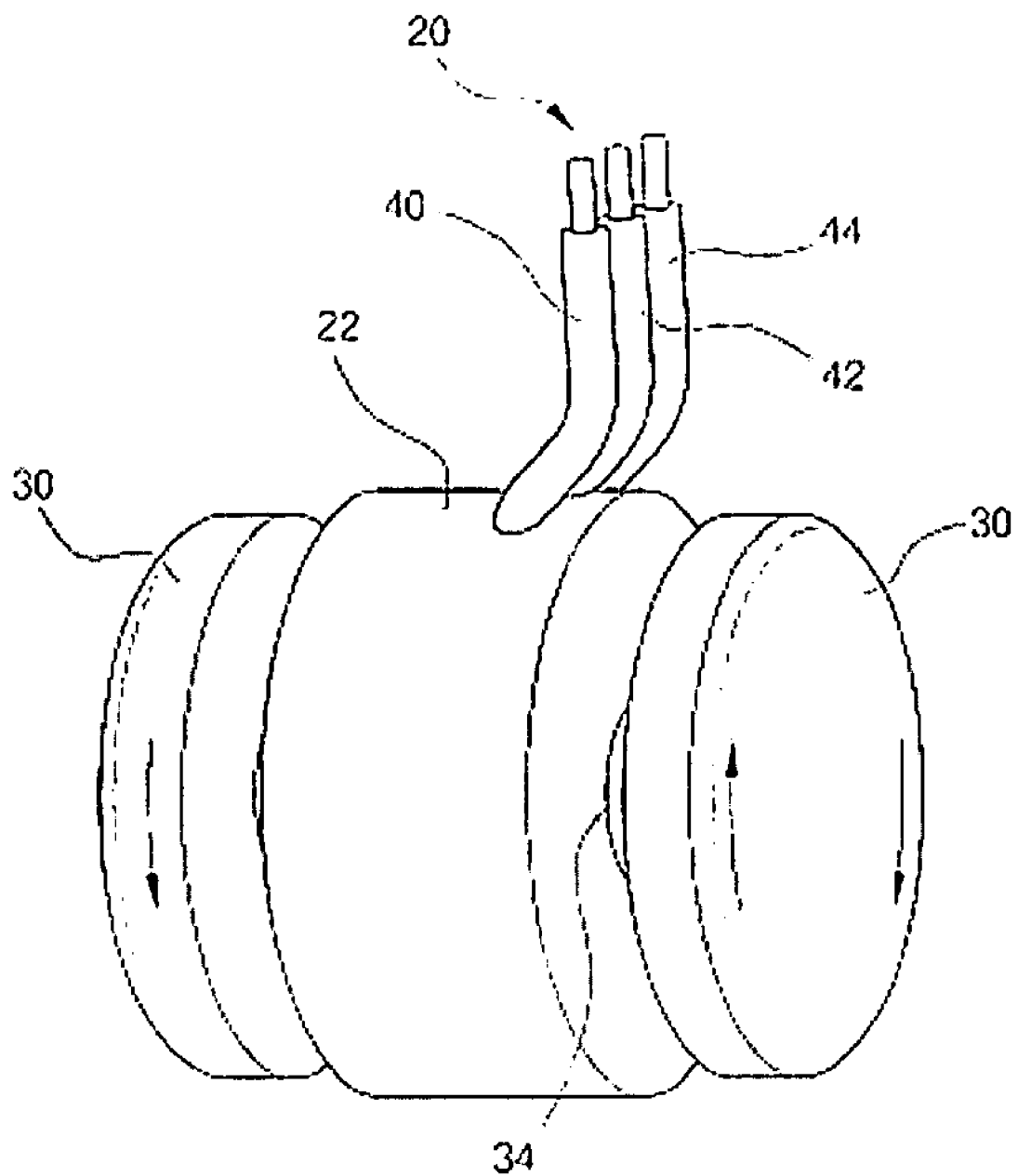
FIG. 2 illustrates an assembly state of a symmetrical viscosity sensor according to an embodiment of the present invention.
Figure 4A:
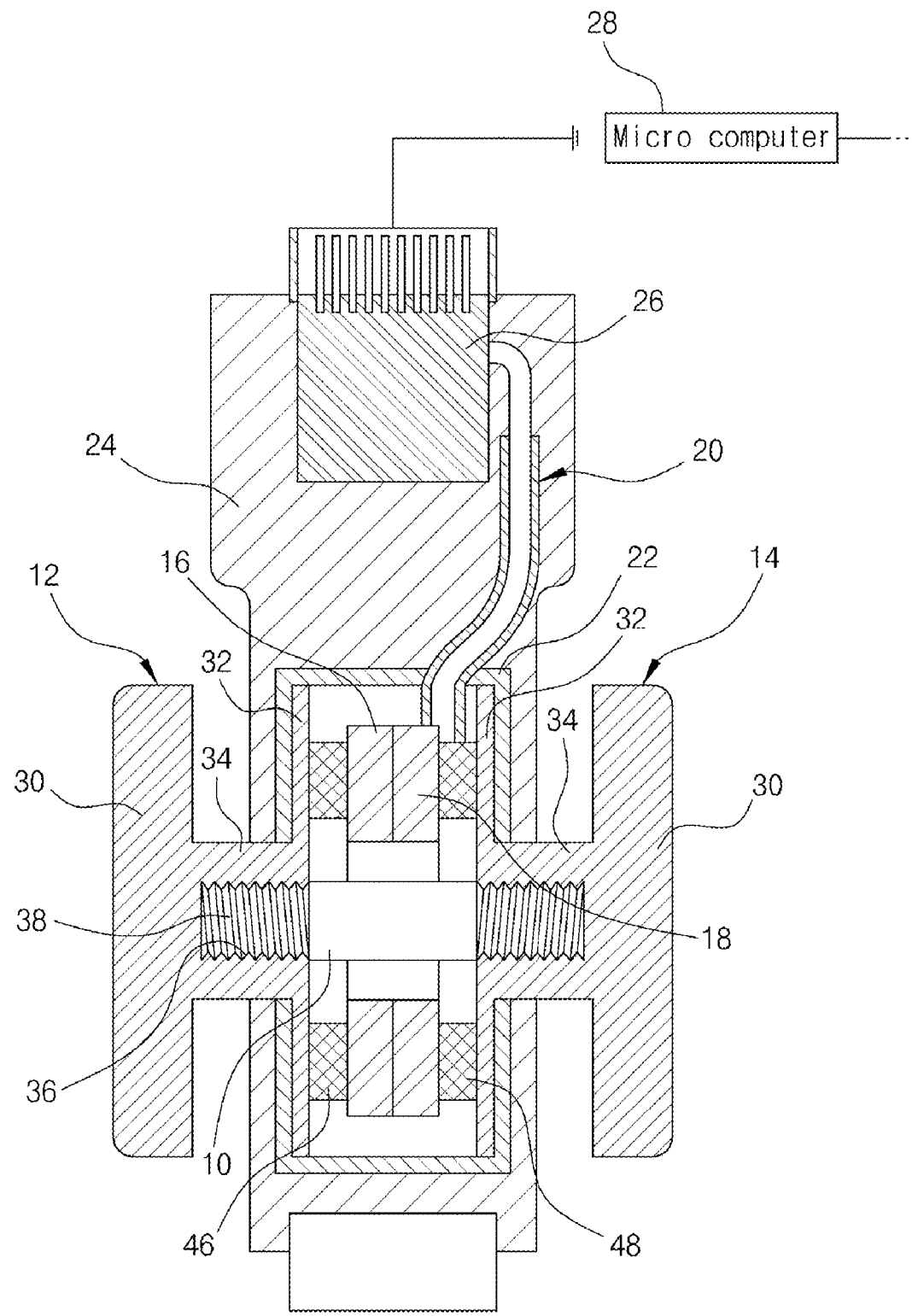
FIG. 4a and FIG. 4b illustrate a mounting state of a symmetrical viscosity sensor according to an embodiment of the present invention.
Figure 4B:
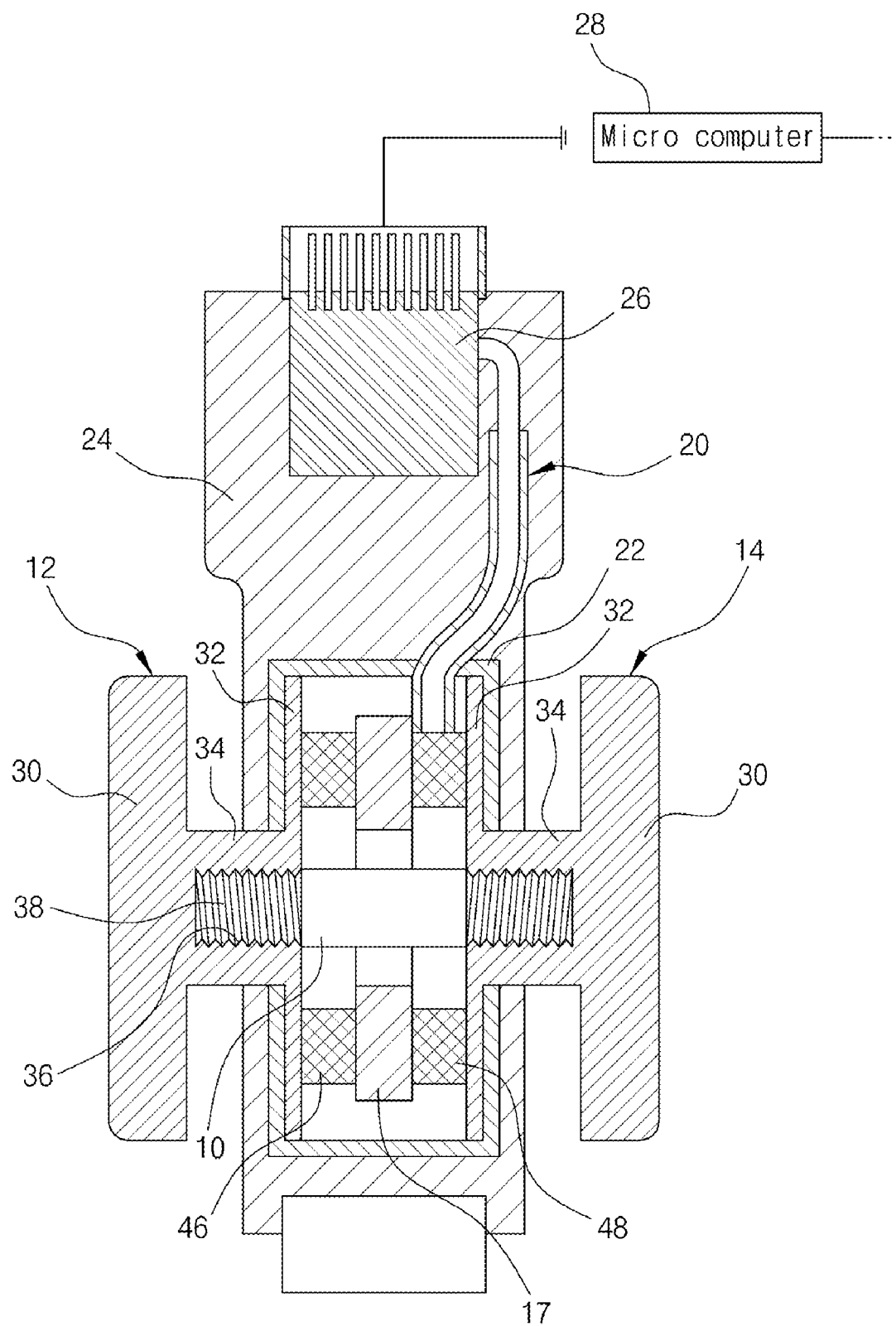

In some embodiments, as shown in FIG. 1b, and FIG. 4b, only one insulator 17 is used.

The oscillation means provides the torsion oscillation to the torsion oscillators 12, 14, and includes a plurality of piezoelectric elements 46 for reception, and piezoelectric elements 48 for transmission.

The plurality of piezoelectric elements 46 for reception are provided between the inside torsion plate 32 of the torsion oscillator 12, and the first insulator 16, and the plurality of piezoelectric elements 48 for transmission are provided between the inside torsion oscillation plate 32 of the torsion oscillator 14, and the second insulator 18.

Four elements with equal spacing may be provided in each piezoelectric element 46, 48.

The inside torsion oscillation plate 32, the insulators 16, 18 and the plurality of piezoelectric elements 46, 48 are surrounded with an inside case 22, and the inside case 22 is surrounded with a case 24.

A printed circuit board 26 is provided on the upper portion of the case 24, and is connected to a microcomputer 28 for exchange of signals.

The printed circuit board 26 and the plurality of piezoelectric elements 46 for reception are connected via a power supply line 40 and a ground line 42 of a signal transmission/reception line 20. Further, the printed circuit board 26 and the plurality of piezoelectric elements 48 for transmission are connected via a signal detection line 44 of the signal transmission/reception line 20.

Figure 3:
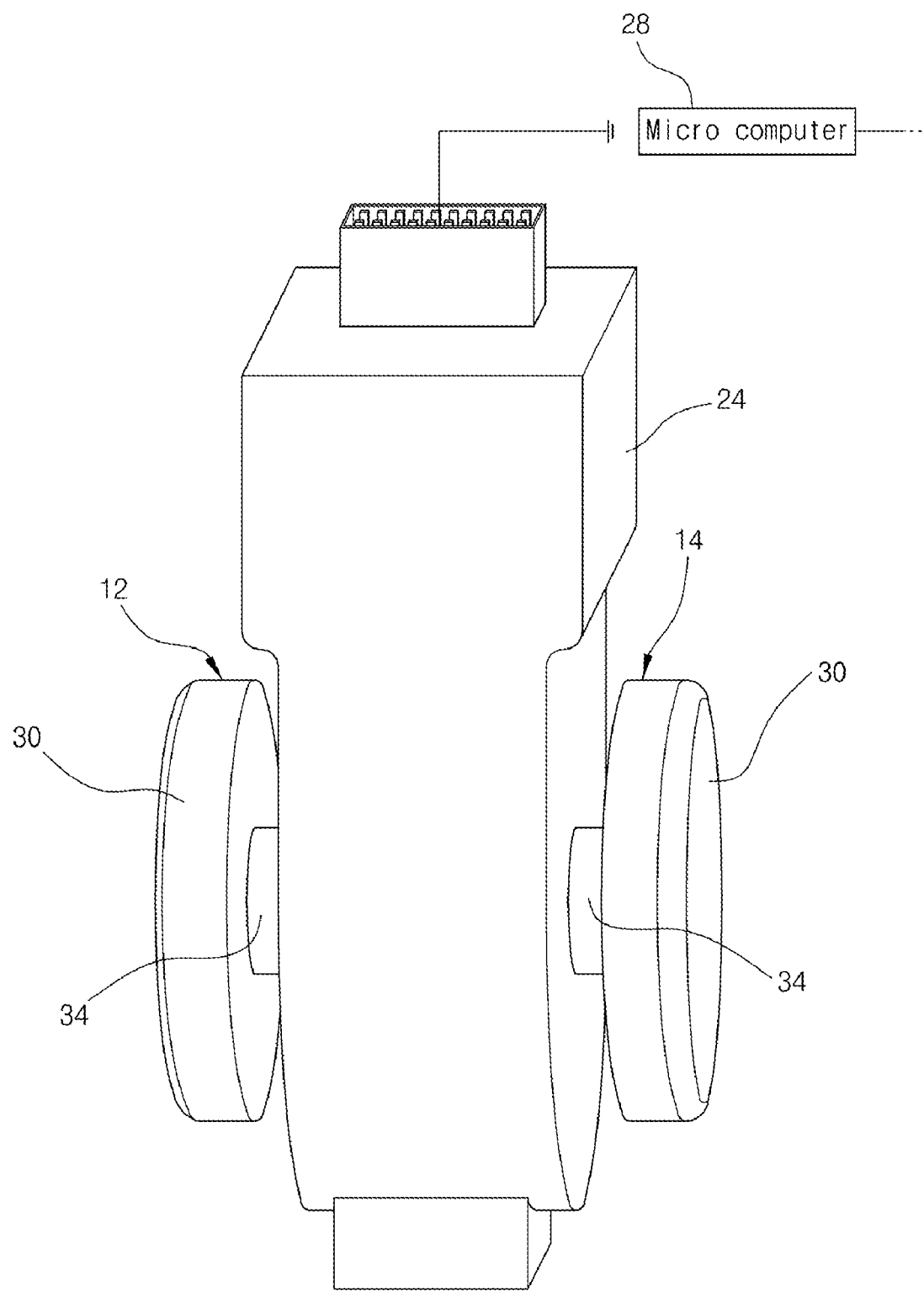
FIG. 3 illustrates a mounting state of a symmetrical viscosity sensor according to an embodiment of the present invention.

As shown in FIG. 3 and FIG. 4, the exterior torsion oscillation plates 30 and the oscillation shaft 34 are exposed to outside of the case 24, and the inside torsion oscillation plate 30 is housed inside the case 22.

Here, the operations of a symmetrical viscosity sensor according to an embodiment of the present invention will be explained.

It is to be noted that the exterior torsion oscillation plates 30 performs a shearing operation, and the torsion oscillators 12, 14 are symmetrical so that influences due to exterior oscillations (oscillations due to an engine, a power generator, a transmission gear, etc.) may be eliminated.

Further, the torsion oscillators 12, 14 move in a symmetrical way around a middle surface of oscillation, and has an inertia equilibrium. Because of the symmetrical structure, the torsional displacement of each oscillator is reversed at a middle portion, thereby the influences due to oscillation of an engine is to be eliminated.

When the driving signal of a microcomputer 28 is transmitted to the piezoelectric elements 46 for reception via the printed circuit board 26 and the power supply line 40, the piezoelectric elements 46 for reception generate torsional oscillation, which is transferred to the exterior torsion oscillation plate 30 via the inside torsion oscillation plate 32, and the osciallation shaft 34.

Therefore, the exterior torsion oscillation plate 30 and the osciallation shaft 34 generate torsional oscillation in the fluids, and the left/right symmetrical movement is generated around the middle surface of oscillation.

Next, the oscillation frequency of the exterior torsion oscillation plate 30 and the osciallation shaft 34 is detected by the plurality of piezoelectric elements 48 for transmission, and the detection signal is transmitted to the microcomputer 28 via the signal detection line 44, and then the printed circuit board 26.

The microcomputer 28 measures the viscosity of the fluids.

Here, a test example of a symmetrical viscosity sensor according to the present invention will be explained.

Figure 5:
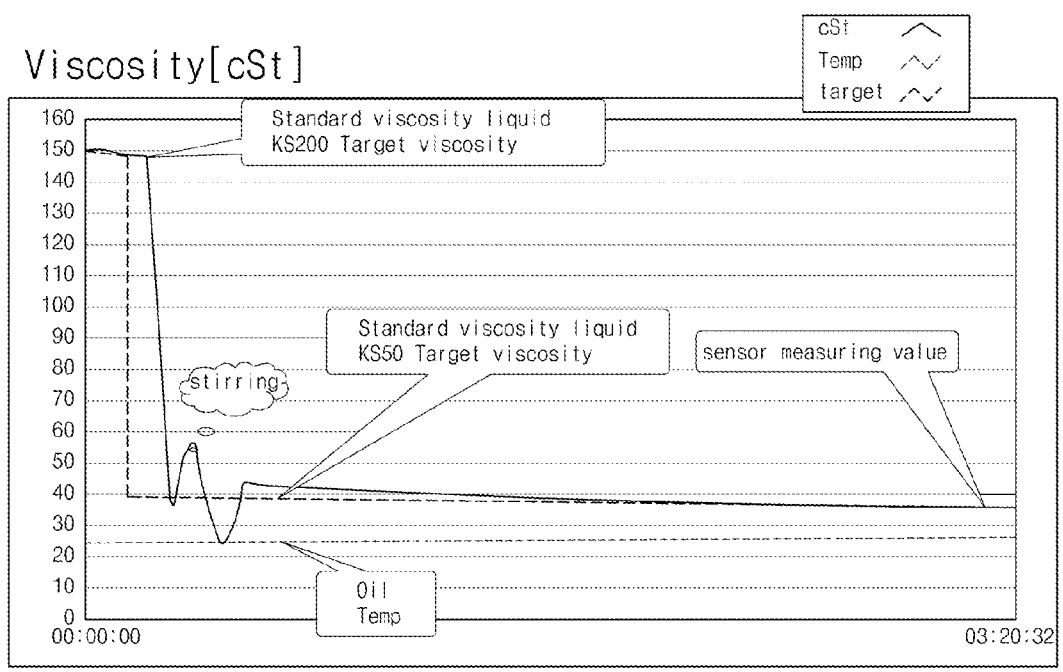
FIG. 5 illustrates measurement results measured in standard viscosity liquid.

FIG. 5 illustrates a test example of a symmetrical viscosity sensor according to the present invention, and is a diagram depicting measurement results measured in standard viscosity liquid.

As shown in FIG. 5, it is to be understood that the computing value (a dotted line) for the standard viscosity of an engine oil, and the value (a solid line) measured by the sensor of the present invention are consistent.

Figure 6:
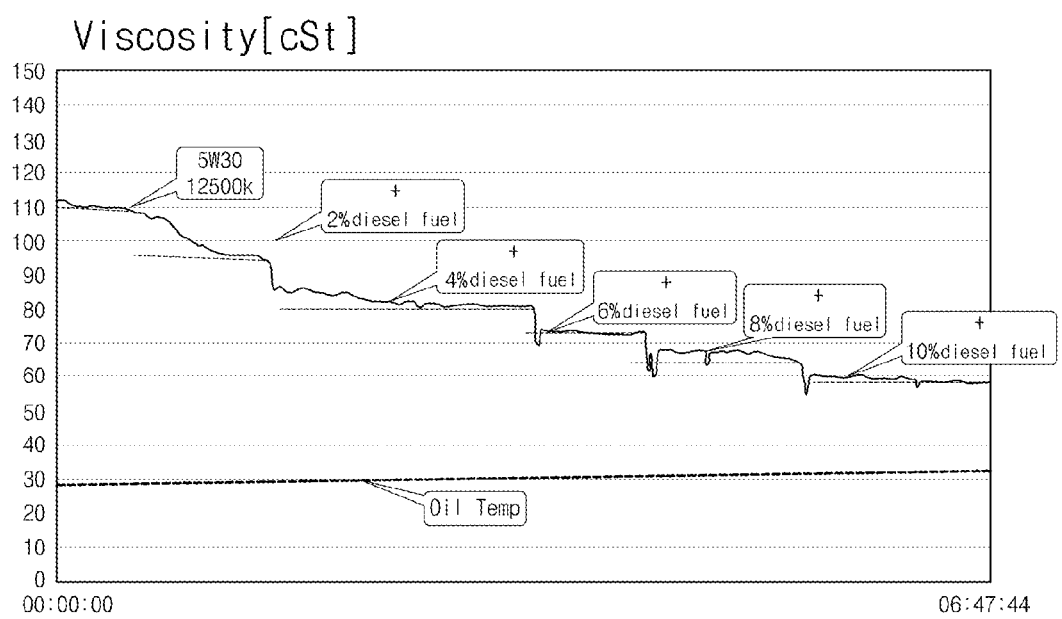
FIG. 6 illustrates change values of viscosity measurement results when gasoline is diluted into an engine oil.

As another test example, when gasoline is diluted into the engine oil, the viscosity is measured, and the results are shown in the graph of FIG. 6.

The measured oil is the degraded engine oil obtained after driving of 12,500 km, and the initial viscosity was measured in a lab room. At every predetermined time interval, gasoline of 2% was added and the viscosity was measured while stirring.

As a result of the measurement, it is found that as the added gasoline increased, so the viscosity decreased remarkably.

Figure 7:
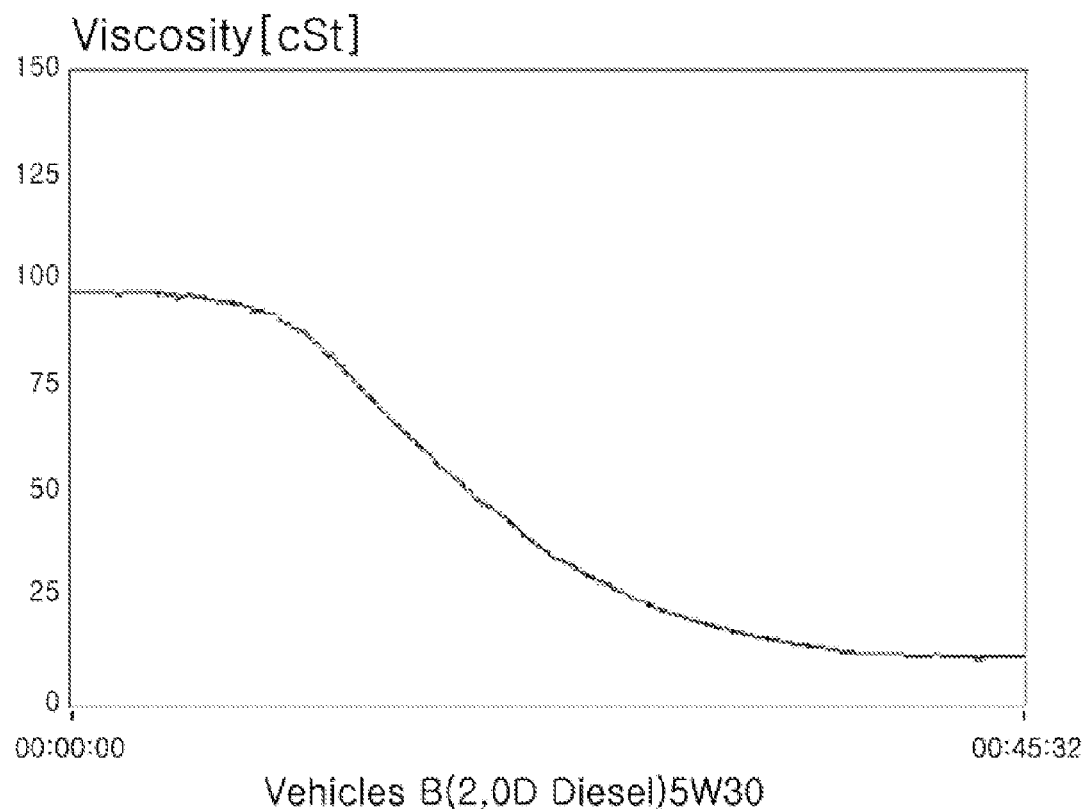
FIG. 7 illustrates viscosity measurement results of an engine oil after the sensor is mounted on a car and the car is started at a normal temperature.

As an another test example, after the viscosity sensor of the present invention was mounted on a car, and the car was started, the viscosity of the engine oil was measured, and the results are shown in the graph of FIG. 7.

As shown in FIG. 7, it is to be understood that as time passes by after starting, the viscosity is decreasing, this phenomenon is ascribed to the increase of temperature of the engine oil, and the viscosity is measured very smoothly in the engine in which oscillation and noises are generated.

Through such a test example, it can be well understood that the viscosity sensor according to the present invention can precisely measure the viscosity of the engine oil.

As described above, the symmetrical viscosity sensor according to the present invention provides following effects.

1) Since the torsion oscillators are arranged symmetrically on both sides, the sensing effective areas increase, and the viscosity can be measured effectively due to oscillations within the elastic range.

2) Since the torsion oscillator for measuring the viscosity generated due to the torsion oscillation is formed as a complete symmetrical structure, it can be always used as a viscosity measuring device in an engine, a power generator, a transmission gear and etc. in which excessive oscillations are generated without influencing a mounting portion.

3) The sensor can be manufactured as a very small device which weighs 10 g, and thus can be used very conveniently.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A symmetrical viscosity sensor, comprising:
    a coupling shaft comprising a first end, a second end, and a center portion;
    a first torsion oscillator coupled to the first end of the coupling shaft;
    a second torsion oscillator coupled to the second end of the coupling shaft;
    at least one insulator coupled to the center portion of the coupling shaft;
    at least one first oscillation means between the first torsion oscillator and the insulator;
    at least one second oscillation means between the second torsion oscillator and the insulator;
    a signal transmission/reception line for transmitting and receiving a driving and detection signal of the first and second oscillation means; and
    a control unit for controlling the driving and detection signal via the signal transmission/reception line,
    wherein the first and second torsion oscillators are geometrically symmetric and configured to be immersed in a fluid.

2. The symmetrical viscosity sensor set forth in claim 1, further comprising a first housing that houses the insulator, the first and second oscillation means, the signal transmission/reception line, and an inner portion of each of the first and second torsion oscillators.

3. The symmetrical viscosity sensor set forth in claim 2, further comprising a second housing surrounding the first housing.

4. The symmetrical viscosity sensor set forth in claim 1, wherein the control unit comprises:
    a circuit board connected to the signal transmission/reception line, and
    a microcomputer for receiving a signal transmitted from the circuit board.

5. The symmetrical viscosity sensor set forth in claim 1, wherein each of the first and second torsion oscillators comprises:
    an exterior torsion oscillation plate;
    an inside torsion oscillation plate; and
    an oscillation shaft which is connected to the exterior torsion oscillation plate and the inside torsion oscillation plate.

6. The symmetrical viscosity sensor set forth in claim 5, wherein each inside torsion oscillation plate comprises a female screw thread and the coupling shaft comprises two ends, each comprising a male screw thread attached to one of the female screw threads.

7. The symmetrical viscosity sensor set forth in claim 1, wherein the signal transmission/reception line comprises:
    a power supply line for driving the oscillation means; and
    a signal detection line for receiving a detection signal of the oscillation means.

8. The symmetrical viscosity sensor set forth in claim 1, wherein:
    the first oscillation means comprises at lease one first piezoelectric element for reception between the insulator and a first of the torsion oscillators, for receiving a signal from the signal transmission/reception line; and
    the second oscillation means comprises at least one second piezoelectric element for transmission between the insulator and a second of the torsion oscillators, for transmitting a signal to the control unit via the signal transmission/reception line.

9. The symmetrical viscosity sensor set forth in the claim 8, wherein the piezoelectric elements are disposed between the torsion oscillator and the insulator.

* * * * *